United States Patent

Itoh et al.

Patent Number: 4,654,177
Date of Patent: Mar. 31, 1987

[54] HYDROXYALKANESULFONIC ACIDS AND THEIR DERIVATIVES AND PROCESS FOR PREPARING SAME

[75] Inventors: Hiroshi Itoh; Atsuhiko Nitta, both of Yokohama; Hideo Kamio, Odawara, all of Japan

[73] Assignee: Mitsui-Toatsu Chemicals, Incorporated, Tokyo, Japan

[21] Appl. No.: 776,797

[22] Filed: Sep. 17, 1985

Related U.S. Application Data

[63] Continuation of Ser. No. 582,573, Feb. 16, 1984, abandoned.

[30] Foreign Application Priority Data

Jun. 12, 1982 [JP]  Japan .................................. 57-102078
Jun. 23, 1982 [JP]  Japan .................................. 57-106711

[51] Int. Cl.$^4$ ............................................ C07C 143/42
[52] U.S. Cl. .................................................. 260/512 R
[58] Field of Search ........................ 260/505 R, 512 R

[56] References Cited

PUBLICATIONS

Gilbert, Sulfonation & Related Reactions, p. 149, (1965).

Kharash et al., J. Am. Chem. Soc., 61, 3092–3098, (1939).

*Primary Examiner*—Alan Siegel
*Attorney, Agent, or Firm*—Fisher, Christen & Sabol

[57] ABSTRACT

Hydroxyalkanesulfonic acids of the general formula

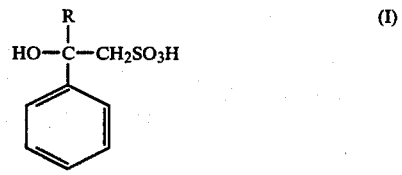

where R is a lower alkyl group having 1 to 10 carbon atoms, and derivatives (such as alkali metal salts and the like) of the sulfonic acids are novel compounds. These compounds can be prepared, for example, by a process which comprises reacting an α-alkylstyrene with the hydrogensulfite ion in an aqueous medium in the presence of oxygen. These compounds are useful as raw materials for the manufacture of amidoalkanesulfonic acid derivatives having such applications as lime soap dispersants, raw materials for the synthesis of water-soluble polymers, fiber modifiers and the like.

2 Claims, No Drawings

HYDROXYALKANESULFONIC ACIDS AND THEIR DERIVATIVES AND PROCESS FOR PREPARING SAME

This is a continuation of application U.S. Ser. No. 582,573 filed Feb. 16, 1984, now abandoned.

DESCRIPTION

1. Technical Field

This invention relates to hydroxyalkanesulfonic acids typified by 2-phenyl-2-hydroxypropanesulfonic acid, and hydroxyalkanesulfonic acid derivatives typified by a sodium salt of the aforesaid acid, as well as a process for preparing these compounds.

2. Background Art

The hydroxyalkanesulfonic acids of the present invention, i.e., the α-hydroxy-β-sulfonic acid derivatives of α-alkylstyrenes, and hydroxyalkanesulfonic acid derivatives such as ammonium, alkali metal and alkaline earth metal salts of such compounds are novel substances which have never been known in the past. The hydroxyalkanesulfonic acid derivatives of the present invention are useful as raw materials for the manufacture of amidoalkanesulfonic acid derivatives (e.g., 2-acrylamido-2-phenylpropanesulfonic acid) having such applications as lime soap dispersants, raw materials for the synthesis of water-soluble polymers, fiber modifiers and the like.

DISCLOSURE OF THE INVENTION

It is an object of the present invention to provide hydroxyalkanesulfonic acids of the general formula

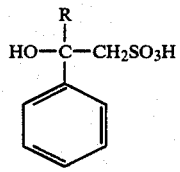

(I)

where R is a lower alkyl group having 1 to 10 carbon atoms, and derivatives thereof which compounds are novel substances and useful as raw materials for the manufacture of amidoalkanesulfonic acid derivatives and the like.

It is another object of the present invention to provide a process for preparing compounds of the above-described general formula (I) and derivatives thereof. According to the present invention, these compounds can be prepared by reacting an α-alkylstyrene with hydrogensulfite ion in an aqueous medium in the presence of oxygen. Moreover, they can be efficiently prepared by using an alkaline earth metal hydrogen-sulfite as the hydrogensulfite ion source substance and initiating the reaction with the sulfite suspended in the reaction mixture.

BRIEF DESCRIPTION OF THE DRAWINGS

FIGS. 1 and 2 are diagrams showing the IR and NMR spectra, respectively, of an exemplary product prepared according to the present invention.

BEST MODE FOR CARRYING OUT THE INVENTION

The hydroxyalkanesulfonic acids of the present invention are represented by the above-described general formula (I) in which R is a lower alkyl group having 1 to 10 carbon atoms. The alkyl group may be straight-chain or branched. The hydroxyalkanesulfonic acid derivatives of the present invention refer to ammonium, alkali metal and alkaline earth metal salts of the hydroxyalkanesulfonic acids represent by the above-described general formula (I). Typical examples of the alkali metal salts include lithium, sodium and potassium salts and typical examples of the alkaline earth metal salts include magnesium, calcium and barium salts.

Typical compounds falling within the scope of the present invention include 2-phenyl-2-hydroxypropanesulfonic acid, 2-phenyl-2-hydroxybutanesulfonic acid, 2-phenyl-2-hydroxy-3-methylbutanesulfonic acid and 2-phenyl-2-hydroxypentanesulfonic acid, as well as ammonium, $Na^+$, $K^+$, $Mg^{2+}$, $Ca^{2+}$, $Ba^{2+}$ and like salts of the foregoing acids.

The compounds of the present invention can be prepared by reacting an α-alkylstyrene with hydrogensulfite ion in an aqueous medium in the presence of oxygen.

As the α-alkylstyrene, there may be used styrene derivatives having a lower alkyl substituent group of 1 to 10 carbon atoms located at the α position of the double bond of the styrene. Specific examples thereof include α-methylstyrene, α-ethylstyrene, α-n-propylstyrene, α-isopropylstyrene and the like.

As the oxygen supplied to the reaction system, there may be used either pure oxygen or an oxygen-containing gas such as air. However, higher oxygen contents of the supplied gas are advantageous in that they permit the reaction to proceed more rapidly.

As the aqueous medium, there may be used any of various types of water such as industrial water or deionized water. Alternatively, a mixture of a water-miscible organic solvent and water can also be used as the aqueous medium. The water-miscible organic solvent can be either a protic solvent such as an alcohol or an aprotic solvent such as acetonitrile, tetrahydrofuran, dioxane, N,N-dimethylformamide, N,N-dimethylacetamide, dimethyl sulfoxide or the like. Since α-alkylstyrenes have low solubility in water, it is advantageous to use a mixed solvent consisting of water and an organic solvent so as to increase the amount of α-alkylstyrene dissolved in the reaction mixture. On the other hand, however, the use of such a mixed solvent is not always economical because the solubility of the hydrogensulfite ion source substance is decreased and, moreover, additional labor is required for the recovery of the solvent and the like.

It is also possible to accelerate the reaction by the addition of various surface active agents or phase transfer catalysts. Usable surface active agents include a variety of cationic, nonionic and anionic surface active agents. Among them, it is preferable to use cationic and nonionic surface active agents. Usable phase transfer catalysts include quaternary ammonium salts such as tetramethylammonium chloride, tetraethylammonium bromide, tetrabutylammonium bromide, benzyltriethylammonium chloride, trioctylmethylammonium chloride and the like.

As the hydrogensulfite ion source substance, there may be used sulfurous acid; alkali metal hydrogensulfites such as ammonium hydrogensulfite, sodium hydrogensulfite, potassium hydrogensulfite, lithium hydrogensulfite; alkaline earth metal hydrogensulfites (obtained by dissolving alkaline earth metal sulfites in aqueous sulfurous acid) such as magnesium hydrogensulfite, calcium hydrogensulfite, barium hydrogensulfite; and the like. Moreover, it is also possible to accelerate the reaction by the addition of transition metal ions (such as Fe, Cu) which form a redox system with hydrogensulfite ion.

In carrying out the reaction, the pH of the reaction mixture is adjusted to a value in the range of 0.2 to 7 and preferably in the range of 0.5 to 6. If the pH is lower than 0.5, the concentration of hydrogensulfite ion in the reaction mixture is decreased, so that the concentration of undissociated sulfurous acid becomes relatively high and the reaction tends to proceed slowly. On the other hand, if the pH is higher than 6, the concentration of sulfite ion becomes relatively high, so that by-products are formed preferentially and the yield of the desired compound tends to decrease. Usually, the pH becomes lower as the reaction proceeds. Whenever the pH becomes 0.5 or less, it should be readjusted by the addition of an alkaline substance such as a hydroxide, carbonate or sulfite of an alkali metal or alkaline earth metal.

The reaction temperature may range from $-20°$ to $70°$ C. and preferably from $-10°$ to $60°$ C. Although the reaction time depends on the reaction temperature, it usually ranges from 20 minutes to 10 hours.

The quantitative relationship between the hydrogensulfite ion and the $\alpha$-alkylstyrene is such that the former is usually present in excess and that they are used in a molar ratio ranging from 1.0 to 20.0 and preferably from 1.5 to 15. The relative proportion of the $\alpha$-alkylstyrene to the aqueous medium is usually such that they are used in a volume ratio ranging from 5/95 to 70/30 and preferably from 5/95 to 60/40.

In accordance with one preferred embodiment, the process of the present invention is carried out by adding the hydrogensulfite ion source substance and the $\alpha$-alkylstyrene to the aqueous medium and reacting the resulting mixture, with stirring, in the presence of oxygen gas or an oxygen-containing gas such as air.

The hydrogensulfite ion source substance may be added in a solid form and then dissolved, or may be dissolved and then added. Since the $\alpha$-alkylstyrene has low solubility in water, the reaction mixture usually forms two clear layers. However, the reaction may be carried out while the reaction mixture is being stirred to suspend the $\alpha$-alkylstyrene in the aqueous medium.

On the other hand, the oxygen may be supplied by blowing a stream of oxygen gas or an oxygen-containing gas through the reaction mixture, or may be supplied under pressure to a closed system. The latter mode of carrying out the reaction in a closed system is advantageous in that it allows the reaction to proceed rapidly. The reaction can be further accelerated by increasing the stirring speed so that the oxygen gas may be more easily absorbed into the reaction mixture and the $\alpha$-alkylstyrene may be more finely dispersed in the aqueous medium. After the reaction is carried out for a predetermined period of time while the reaction is being followed, the desired 2-phenyl-2-hydroxyalkanesulfonic acid salt is separated.

The reaction can be followed, for example, by tracing the supply of oxygen, the disappearance of the 2-alkylstyrene or the formation of the desired compound with the aid of a gas flowmeter, gas chromatograph or high-speed liquid chromatograph. The desired compound can usually be separated, for example, by cooling the reaction mixture and allowing it to stand until crystallization takes place; by distilling off the aqueous medium from the reaction mixture and recrystallizing the residue from a polar solvent such as water or water-containing alcohol; or by passing the reaction mixture through an ion exchange resin such as a strongly acidic cationic exchange resin in the hydrogen form and adding an alkaline earth metal hydroxide or carbonate to the effluent so as to remove any unreacted sulfite radical and formed sulfate radical and thereby obtain the desired compound in the form of an aqueous solution.

The type of the cation which constitutes the counter ion present in each of the sulfinic acid salts of the present invention can be determined either by using a specific counter ion for the hydrogensulfite ion to be reacted with or by passing the reaction mixture through a strongly acidic cation exchange resin in the hydrogen form and neutralizing the resulting effluent with a specific alkali. Moreover, the type of the cation can also be determined by introducing a desired cation into a cation exchange resin and then passing the reaction mixture through the cation exchange resin.

In the hydroxyalkanesulfonic acid salts prepared according to the above-described procedure, there may be present a 2-phenyl-2-sulfatoalkane-1-sulfonic acid salt formed as a by-product. However, this compound can be converted into the desired compound by hydrolyzing it with an acid or alkali. Moreover, where used as a raw material for the manufacture of an amidoalkanesulfonic acid derivative, such a hydroxyalkanesulfonic acid salt containing the above-described by-product can be used without any difficulty to produce the desired amidoalkanesulfonic acid derivative.

Upon closer investigation of the basic process for the preparation of the above-described hydroxyalkanesulfonic acids and their derivatives in accordance with the present invention, i.e., the process involving the reaction of an oily layer of an $\alpha$-alkylstyrene with an aqueous medium layer having hydrogensulfite ion dissolved therein, the following three major problems have been revealed Specifically, the first problem is that, as stated before, the pH of the reaction mixture becomes lower as the reaction proceeds. This is due to an increase of hydrogensulfate ion formed as a by-product during the reaction, which results in a decreased hydrogensulfite ion concentration and, hence, a reduced reaction rate. Accordingly, pH adjustment must be made, for example, by the addition of an alkali so that the reaction may proceed rapidly. However, this procedure is troublesome in most cases.

The second problem is the low solubility of the $\alpha$-alkylstyrene in water. In order to allow the reaction to proceed rapidly, it is necessary to disperse the $\alpha$-alkylstyrene in a finely divided state or enhance the solubility of the $\alpha$-alkylstyrene in the aqueous medium by the addition of a third substance. Generally, this can be accomplished by carrying out the reaction with any of the aforesaid surface active agents and phase transfer catalysts added to the reaction mixture or by carrying out the reaction in a mixture of a water-miscible organic solvent and water. However, there will arise new problems including an increase in production cost due to the addition of the third substance, the necessity for separating the desired compound from the third substance and, further, the necessity for recovering the added solvent.

The third problem is concerned with the separation of the desired compound. Since the reaction mixture contains hydrogensulfite ion and hydrogen-sulfate ion formed as a by-product and these ions are not volatile, the desired compound is liable to contamination with these substances. In order to minimize such contamination, it is conceivable to purify the desired compound by recrystallization or treatment with an ion exchange resin. In the case of recrystallization, however, the absence of a marked difference in solubility between the contaminants and the desired compound dictates repeated recrystallization to result in a decrease in the yield of the product. As for the use of an ion exchange resin, since the contaminants and the desired compound are both ionic substances, an immense quantity of ion exchange resin is required to result in an increase in production cost.

The present inventors have found that the above-described problems can be overcome by employing a process which involves initiating the aforesaid reaction with an alkaline earth metal sulfite suspended in the reaction mixture (hereinafter referred to as the improved process). This improved process makes it possible to facilitate the pH adjustment of the reaction mixture, to keep the α-alkylstyrene well dispersed in the aqueous medium, especially at the beginning of the reaction, and to separate the desired compound in a highly pure form.

More specifically, when an alkaline earth metal sulfite is suspended in the reaction mixture, the hydrogensulfate ion causative of a reduction in pH reacts with the sulfite to form a sulfate which precipitates from the reaction mixture because of its low solubility in water. On the other hand, the reaction regenerates hydrogensulfite ion and, as a result, the disappearance of hydrogensulfite ion associated with the formation of hydrogensulfate ion is compensated. Moreover, the oily α-alkylstyrene layer is very well dispersed by suspending the alkaline earth metal sulfite in the reaction mixture. The reaction mixture immediately separates into two layers in the absence of sulfite, whereas the suspension of the sulfite greatly slows down the separation into two layers because the suspensoid stabilizes the oil droplets of the α-alkylstyrene.

Where calcium or barium ion is used as the alkaline earth metal ion and the reaction is stopped by adding an oxide, hydroxide or carbonate thereof to the reaction mixture and thereby bringing its pH to neutrality, the hydrogensulfite and hydrogensulfate ions present in the reaction mixture are converted into the corresponding sulfite and sulfate having low solubility in water. This sulfite and sulfate can be separated as a precipitate from the aqueous solution, so that the desired compound of high purity can be obtained in the aqueous solution.

It is also possible to carry out the reaction with any of various surface active agents and phase transfer catalysts added to the reaction mixture. However, this improved process permits the intended purpose to be satisfactorily accomplished without addition of such a third component.

The aforesaid improved process is described hereinbelow in more detail. Although any alkaline earth metal ion may be used in this improved process, the use of calcium or barium ion is particularly preferred. Alakaline earth metal hydrogensulfites exist only in aqueous solution in the presence of free sulfurous acid. Accordingly, alkaline earth metal hydrogensulfites may be prepared either by adding a sulfite to an aqueous solution of sulfurous acid or by blowing sulfur dioxide through an aqueous solution having a sulfite suspended therein. In order to bring the sulfite into a partially suspended state, it is preferable to add sulfurous acid usually in an amount less than or equal to ten times the moles of the sulfite, depending on the type of the alkaline earth metal ion and the concentration of sulfurous acid. The sulfite used as a starting material may be prepared by any of various procedures including the neutralization of an alkaline earth metal hydroxide or oxide with sulfurous acid, the reaction of an alkaline earth metal carbonate with sulfurous acid, and the double decomposition of an alkali metal sulfite and an alkaline earth metal chloride. Especially in the first case, after a specified amount of sulfurous acid is added and before the neutralization of the hydroxide or oxide with the sulfurous acid is not completed, an α-alkylstyrene may be added to carry out the reaction of the present invention.

In order to carry out this improved process in a preferable manner, an alkaline earth metal sulfite, carbonate, hydroxide or oxide is suspended in an aqueous medium and sulfur dioxide or aqueous sulfurous acid is added thereto. Alternatively, an alkaline earth metal sulfite, carbonate, hydroxide or oxide is suspended in aqueous sulfurous acid. Thereafter, the reaction is initiated by adding α-methylstyrene to the aqueous medium containing the hydrogensulfite ion so formed and then introducing an oxygen-containing gas thereinto. On this occasion, it is preferable to initiate the reaction with the alkaline earth metal sulfite suspended in the reaction mixture because this brings the α-alkylstyrene into a well-dispersed state and allows the reaction to proceed rapidly.

The desired compound may be separated by filtering the reaction mixture to remove any suspended matter, adjusting the pH of the filtrate to 4–10 by the addition of an alkaline earth metal oxide, hydroxide or carbonate, filtering the mixture to remove any insoluble matter, and then distilling off the aqueous medium from the filtrate to obtain the desired compound of high purity as the residue. In the above-described procedure, the alkaline earth metal oxide, hydroxide or carbonate may be added to the reaction mixture prior to its filtration.

The desired compound so separated may be directly used as a raw material for the synthesis of amidoalkanesulfonic acids. If it is desired to purify the compound further and use it in a purer form, this can be accomplished, for example, by recrystallizing it from a polar solvent such as water or water-containing alcohol, or by passing the reaction mixture through an ion exchange resin such as a strongly acidic cation exchange resin in the hydrogen form and adding an alkaline earth metal hydroxide or carbonate to the effluent.

In this improved process, the counter ion present in the desired sulfonic acid salt corresponds to the alkaline earth metal ion. If it is desired to change it into an alkali metal ion, this can be accomplished by using a hydroxide, oxide, carbonate or like compound containing the alkali metal ion as the basic substance added to the reaction mixture at the time of stoppage of the reaction. If it is desired to change it into another ion including an alkali metal ion, this can be accomplished, for example, by passing the reaction mixture through a strongly acidic cation exchange resin in the hydrogen form and neutralizing the effluent with a specific alkaline substance; by introducing a desired cation into a cation exchange resin and passing the reaction mixture through the cation exchange resin; or by subjecting the product thus obtained and a sulfate to double decomposition.

The present invention is further illustrated by the following examples.

EXAMPLE 1

Into a 2-liter round bottom flask were charged 374 g of sodium hydrogensulfite and 1.2 liters of water. After the atmosphere within the flask was replaced by oxygen with stirring of its contents, 192 g of α-methylstyrene was added thereto and the resulting mixture was reacted at 50° C. for 10 hours with stirring at a speed of 1,000 rpm. The reaction was carried out in a closed system to which oxygen was supplied so that the pressure within the flask was 10 mmHg higher than the atmospheric pressure.

During this period, the pH of the reaction mixture lowered to 0.5.or less,at which time an aqueous solution of sodium hydroxide was added to keep the pH above 0.5. This procedure was repeated ten times until the reaction was completed. Crystallization was effected by allowing the reaction mixture to stand overnight in an ice bath. Thus, there was obtained 522 g of crystals containing 32% of sodium sulfate. When these crystals were recrystallized from water, there was obtained 310 g (73% yield) of white crystals having a sodium sulfate content of 9%. This substance was subjected to infrared absorption spectrophotometry and nuclear magnetic resonance spectrometry, and the results thus obtained are shown in FIGS. 1 and 2, respectively.

Subsequently, 5.0 g of the aforesaid white crystals and 3.0 g of benzylamine hydrochloride were added to and dissolved in 10 c.c. of distilled water. Thereafter, the water was distilled off to obtain 8.0 g of a white solid material. This solid material was added to 15 c.c. of ethyl alcohol and the resulting mixture was heated under reflux for an hour. While hot, the mixture was filtered through a creased filter paper to remove any insoluble solid matter. The filtrate was further concentrated by heating and then allowed to cool, so that crystals were precipitated. These crystals were separated by filtration to obtain 5.5 g (80% yield) of a benzylamine derivative in the form of white crystals. Elemental analysis of this benzylamine salt, which was assumed to have the formula

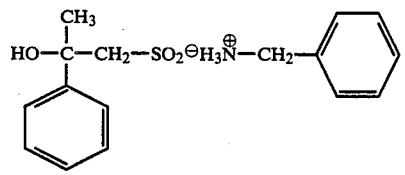

($C_{16}H_{21}NO_4S$), and measurement of its melting point gave the following results.

| | Elemental analysis (%): | | | |
|---|---|---|---|---|
| | C | H | N | S |
| Calculated | 59.44 | 6.50 | 4.33 | 9.91 |
| Found | 58.50 | 6.60 | 4.09 | 10.26 |

Melting point: 139°–140° C.

On the basis of the above-described analytical results, it was determined that the compound obtained by the reaction of α-methylstyrene with sodium hydrogensulfite was 2-phenyl-2-hydroxypropane-1-sulfonic acid sodium salt having the structure represented by the formula

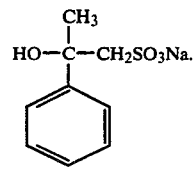

EXAMPLE 2

Reaction was carried out in the same manner as in Example 1 except that the pH of the reaction mixture was adjust to 0.4 with sulfuric acid. Thus, there was obtained 25 g (6% yield) of the desired compound.

EXAMPLE 3

Reaction was carried out in the same manner as in Example 1, except that the pH of the reaction mixture was adjusted to 7 with sodium hydroxide. Thus, there was obtained 260 g of a white substance. The infrared absorption spectrum and nuclear magnetic resonance spectrum of this substance exhibited additional absorption peaks besides those of the desired compound, indicating the presence of some by-products.

EXAMPLE 4

Reaction was carried out in the same manner as in Example 1, except that one drop of a 10% aqueous solution of copper sulfate was added to the reaction mixture. Thus, there was obtained 306 g (72% yield) of the described compound

EXAMPLE 5

28 g of 2-phenyl-2-hydroxypropanesulfonic acid sodium salt was dissolved in 300 ml of water. The resulting aqueous solution was subjected to an ion exchange by passing it through 300 ml of a strongly acidic cation exchange resin in the hydrogen form at a space velocity of 3 hr$^{-1}$.

The effluent was divided into two equal parts. From one of them, the water was directly distilled off to obtain 11 g of 2-phenyl-2-hydroxypropanesulfonic acid.

To the other part was added 15 g of calcium carbonate. After adequate stirring, any insoluble matter was removed by filtration to obtain 2-phenyl-2-hydroxypropanesulfonic acid calcium salt in aqueous solution. This aqueous solution was evaporated to dryness, so that there was obtained 11 g of 2-phenyl-2-hydroxypropanesulfonic acid calcium salt.

EXAMPLE 6

Into a 2-liter round bottom flask were charged 364 g of calcium sulfite and 1 liter of 6% aqueous sulfurous acid. After the atmosphere within the flask was replaced by oxygen with stirring of its contents, 105 g of α-methylstyrene was added thereto. While the calcium sulfite was being suspended with stirring at a speed of 1,000 rpm, the reaction was initiated at 30° C. and continued for 5 hours. The reaction was carried out in a closed system to which oxygen was supplied so that the pressure within the flask was 10 mmHg higher than the atmospheric pressure During this period, the pH of the reaction mixture lowered to 0.5 or less, at which time calcium hydroxide was added to keep the pH above 0.5. This procedure was repeated three times until the reaction was completed.

After the reaction mixture was filtered to remove any insoluble matter, the pH of the resulting solution was adjusted to 5 by the addition of calcium hydroxide. After the solution was filtered again to remove any insoluble matter, the water was distilled off from the filtrate to obtain 184 g (88% yield) of 2-phenyl-2-hydroxypropanesulfonic acid calcium salt.

EXAMPLE 7

Into a 2-liter round bottom flask were charged 11 g of calcium sulfite and 1 liter of 6% aqueous sulfurous acid. After the atmosphere within the flask was replaced by oxygen with stirring of its contents, 30 g of α-methylstyrene was added thereto and the resulting mixture was reacted at 30° C. for 5 hours with stirring at a speed of 1,000 rpm. The reaction mixture consisted of two clear layers, i.e., an oily layer and an aqueous layer. While the oily layer was being suspended in the aqueous layer, the reaction was carried out in a closed system to which oxygen was supplied so that the pressure within the flask was 10 mmHg higher than the atmospheric pressure.

During this period, the pH of the reaction mixture lowered to 0.5 or less, at which time calcium hydroxide was added to keep the pH above 0.5. This procedure was repeated seven times until the reaction was stopped.

After the reaction mixture was filtered to remove any insoluble matter, the water distilled off from the filtrate to obtain 44 g (61% yield) of 2-phenyl-2-hydroxypropanesulfonic acid calcium salt.

EXAMPLE 8

Into a 2-liter round bottom flask were charged 209 g of calcium hydroxide and 1 liter of deionized water. After the atmosphere within the flask was replaced by oxygen with stirring of its contents, 240 g of sulfur dioxide was blown therethrough. Upon completion of the blowing, 105 g of α-methylstyrene was added thereto and the resulting mixture was reacted at 30° C. for 5 hours with stirring at a speed of 1,000 rpm.

The reaction was carried out in a closed system to which oxygen was supplied so that the pressure within the flask was 10 mmHg higher than the atmospheric pressure.

During this period, the pH of the reaction mixture lowered from 2 to 0.8. However, no pH adjustment was made because the pH remained above 0.5 throughout the reaction.

Thereafter, the reaction mixture was worked up in the same manner as in Example 6 to obtain 188 g (90% yield) of 2-phenyl-2-hydroxypropanesulfonic acid calcium salt, the desired compounds.

EXAMPLE 9

Reaction was carried out in the same manner as in Example 6, except that the pH of the reaction mixture was adjusted to 0.15 with sulfuric acid and no further pH adjustment was made. Thus, there was obtained 15 g (7% yield) of the desired compound.

EXAMPLE 10

Reaction was carried out for 3 hours in the same manner as in Example 6, except that one drop of a 10% aqueous solution of copper sulfate was added to the reaction mixture. Thus, there was obtained 194 g (92% yield) of the desired compound.

EXAMPLE 11

Into a 2-liter round bottom flask were charged 612 g of barium sulfite and 1 liter of deionized water. After the atmosphere within the flask was replaced by oxygen with stirring of its contents, 72 g of sulfur dioxide was blown therethrough. After that, 105 g of α-methylstyrene was added thereto and the resulting mixture was reacted at 30° C. for 5 hours with stirring at a speed of 1,000 rpm. Thereafter, the reaction mixture was worked up in all the same manner as in Example 1 to obtain 227 g (90% yield) of 2-phenyl-2-hydroxypropanesulfonic acid barium salt.

EXAMPLE 12

Reaction was carried out in the same manner as in Example 8. Upon completion of the 5 hours' reaction, 65 g of a 50% sodium hydroxide solution and 10 g of calcium carbonate were added to the reaction mixture to confirm that its pH was above 4. After the reaction mixture was filtered to remove any insoluble matter, the water was distilled off from the filtrate to obtain 192 g (91% yield) of 2-phenyl-2-hydroxypropanesulfonic acid sodium salt.

We claim:

1. A process for preparing 2-phenyl-2-hydroxy-propane-1-sulfonic acid of the formula:

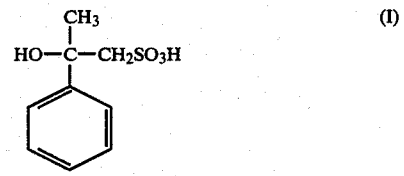

comprising:
reacting alpha-methylstyrene with hydrogensulfite ion in an aqueous medium in the presence of oxygen, said reaction proceeding in a suspended state of calcium sulfite or barium sulfite in said aqueous medium, said aqueous medium being at a pH between 0.2 and 7.0 and at a temperature between −20° C. and 70° C., and wherein the hydrogensulfite ion is used in an amount of between 1.0 and 20 moles per mole of alpha-methylstyrene.

2. A process as claimed in claim 1 wherein a volume ratio of the alpha-methylstyrene to the aqueous medium is between about 5/95 and about 70/30.

* * * * *